United States Patent [19]

Wang

[11] Patent Number: 4,766,257
[45] Date of Patent: Aug. 23, 1988

[54] PREPARATION OF NITRO COMPOUNDS BY VAPOR PHASE NITRATION OF OLEFINS

[75] Inventor: Shu-Chieh P. Wang, Columbia, Md.

[73] Assignee: W. R. Grace & Co., New York, N.Y.

[21] Appl. No.: 849,765

[22] Filed: Sep. 12, 1984

[51] Int. Cl.$^4$ .................. C07C 79/04; C07C 79/06
[52] U.S. Cl. .................................. 568/948; 568/947; 260/688
[58] Field of Search ............... 568/939, 947, 948, 924, 568/943, 927; 260/688

[56] References Cited

U.S. PATENT DOCUMENTS

| | | | |
|---|---|---|---|
| 2,472,550 | 6/1949 | Smith et al. | 568/944 |
| 2,867,669 | 1/1959 | Burkhard et al. | 568/948 |
| 2,894,041 | 7/1959 | Berg | 568/948 |
| 2,999,119 | 9/1961 | McKinnis | 568/947 |
| 3,240,823 | 3/1966 | Bonetti et al. | 568/947 |
| 3,297,769 | 1/1967 | Michalski | 568/947 |
| 3,706,808 | 12/1972 | Bachman et al. | 568/944 |
| 3,780,115 | 12/1973 | Lhonore et al. | |
| 3,869,253 | 3/1975 | Lhonore et al. | |
| 4,260,838 | 4/1981 | Lhonore et al. | |
| 4,313,010 | 1/1982 | Lhonore et al. | 568/948 |
| 4,469,904 | 9/1984 | Wang et al. | 568/948 |
| 4,517,392 | 5/1985 | Wang et al. | 568/948 |
| 4,517,393 | 5/1985 | Wang et al. | 568/948 |
| 4,517,394 | 5/1985 | Wang et al. | 568/948 |
| 4,524,226 | 6/1985 | Wang et al. | 568/948 |
| 4,533,776 | 8/1985 | Baasner . | |
| 4,626,607 | 12/1986 | Jacquinot et al. | 568/948 |

FOREIGN PATENT DOCUMENTS 2106265  4/1972  France .

OTHER PUBLICATIONS

Mardanov et al., CA 71(26):126836m.
Nakahara et al., CA 91(9):74158h.
Slebodzinski et al., CA 74(21):111500k.
Watanabe et al.; CA 88(24):180197t.
Schmitt et al.; CA 95(15):131941s.

*Primary Examiner*—John F. Terapane
*Assistant Examiner*—Eric Jorgensen
*Attorney, Agent, or Firm*—Howard J. Troffkin

[57] ABSTRACT

A process for selectively forming nitrohydrocarbon compounds by contacting, at elevated temperature and pressure and in a homogeneous gas phase, an olefinic unsaturated compound having at least three carbon atoms with NO$_2$ alone or in the presence of oxygen and/or water.

24 Claims, 1 Drawing Sheet

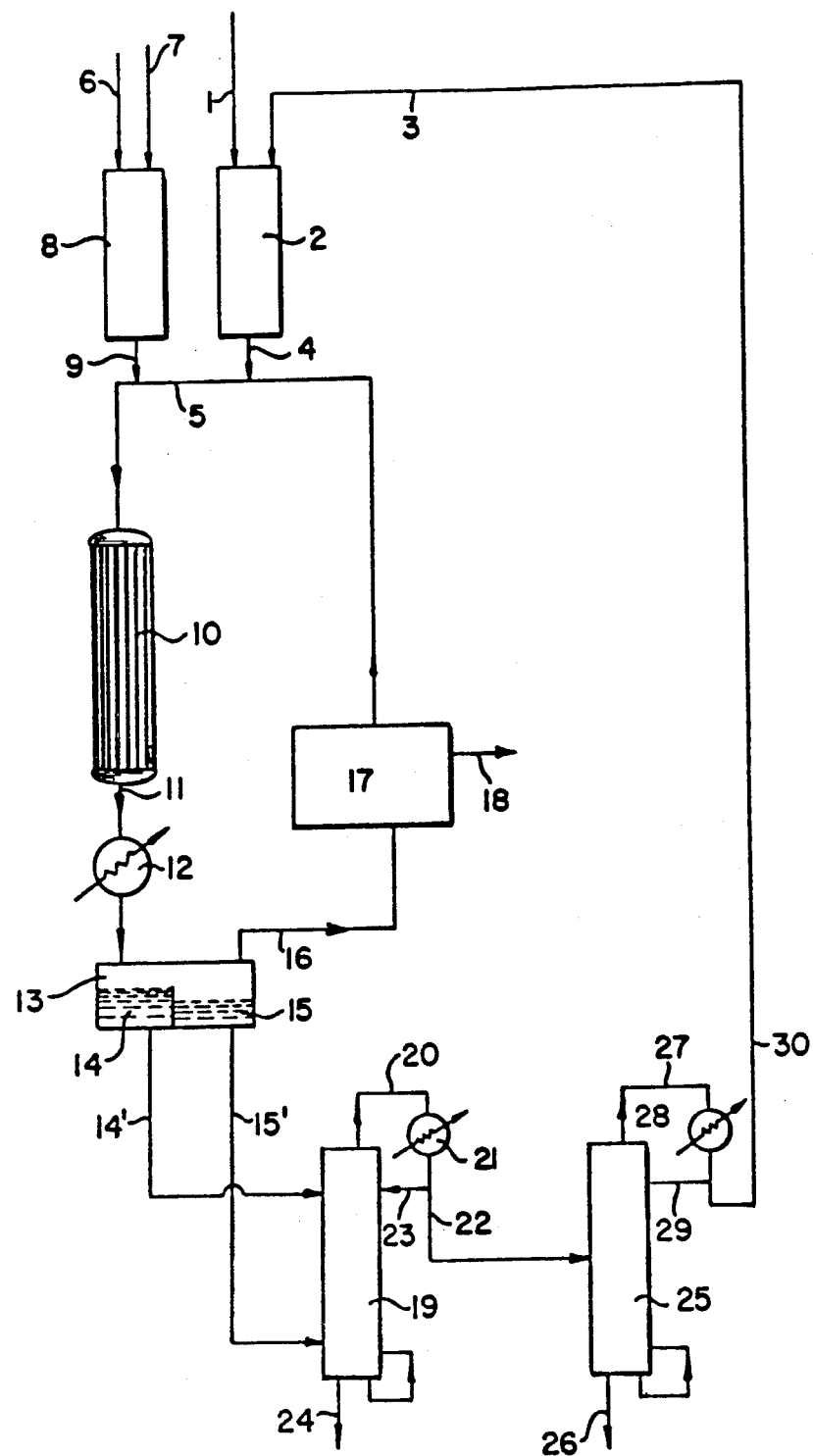

PREPARATION OF NITRO COMPOUNDS BY VAPOR PHASE NITRATION OF OLEFINS

BACKGROUND OF THE INVENTION

The present invention is directed to a process of forming a nitroparaffin and nitroaromatic compounds by gaseous phase reaction of an organic olefinic unsaturated hydrocarbon with $NO_2$. The present process provides a method to form pre-selected nitro compounds based on the particular olefin unsaturated hydrocarbon feed.

Processes to form nitroparaffins by gaseous phase nitration are known. U.S. Pat. Nos. 3,780,115 and 3,869,253 teach that nitration of saturated hydrocarbons higher than methane can be accomplished by contacting the hydrocarbon feed with nitrogen dioxide in the presence of oxygen, such as in the form of air. The reactant gases are preheated and then introduced into the reaction zone where the gaseous phase nitration is carried out at elevated pressure and at elevated temperature. The gaseous effluent emitted from the nitration reaction zone is rapidly quenched. The quenched mixture then enters a separator where the gaseous materials in the form of unreacted hydrocarbon, nitric oxide, carbon monoxide and carbon dioxide are removed for subsequent purification and recycling and the remaining phase liquid materials are separated by decantation and the nitroparaffins are recovered by distillation. This nitration process yields a mixture of products which require further separation and purification.

French Publication No. 78/32,118 discloses that the nitroparaffins product mixture can be made to have an increased yield of nitromethane, the most commercially desired product, by utilizing ethane as the hydrocarbon feed in the homogeneous gas phase nitration. The nitration process can be further enhanced by recycling into the hydrocarbon feed some of the nitropropane product and/or by conducting the nitration in the presence of an inert gas such as nitrogen, hydrogen or argon.

U.S. Pat. No. 4,260,838, similar to the above French reference, teaches that the gas phase nitration process of U.S. Pat. Nos. 3,780,115 and 3,869,253 can be improved by altering the feed stock to obtain suitable percentages of different nitroparaffins as suits the needs of the marketplace. This patent teaches that the feed stock be made up of a mixture containing preferably recycled nitroparaffin and possibly inert gas and/or another alkane. The nitrating agent can be either nitrogen dioxide or nitric acid.

Each of the conventional processes, as described in the above referenced patents, relies on the use of a saturated hydrocarbon feed which provides a nitroparaffin product mixture. These processes have the further defect of providing low yield of nitroparaffin mixture and low selectivity of the most commercially desired compound, nitromethane.

The nitration of olefins has been previously suggested in U.S. Pat. Nos. 2,402,315; 2,472,550; and 2,999,119. The early patents teach that olefins will react with $N_2O_4$ in the presence of a liquid solvent, such as ether to give dinitrogenated addition products which, when hydrolyzed, would form nitroalkanes. Large amounts of by-products of little value were formed. In '119 one is directed to carry out the reaction at low temperatures in an aromatic solvent and to rapidly remove the product from the nitrating agent in order to enhance the yield of nitroalkane. These solution processes have not met great acceptability because they are multistep reactions, require the use of a liquid solvent from which the products must be separated and provide the desired nitroalkanes as a mixture along with large amounts of degraded products.

A method to selectively form particular nitroalkanes from easily available and processable feed is highly desired. It is particularly desired to have a process to selectively form nitromethane, a very industrially useful product.

SUMMARY OF THE INVENTION

An object of the present invention is to provide a process by which a selective nitroparaffin can be formed or that a selective nitro compound is the predominant compound of the resultant products.

Another object of the present invention is to provide a process by which the various unreacted feed materials are readily separated and recyclable.

Another object of the present invention is to provide a process by which one can selectively form nitromethane from readily available and processable materials.

The process of the present invention is capable of selectively forming particular nitrohydrocarbon compounds by contacting at elevated temperatures and pressures in a homogeneous gas phase a $C_3$ to $C_{10}$ olefinic unsaturated hydrocarbon with $NO_2$ preferably in the presence of oxygen and/or water.

DETAILED DESCRIPTION OF INVENTION

A process for selectively forming particular nitrohydrocarbon compounds comprises contacting under homogenous gas phase reaction conditions an olefinic unsaturated hydrocarbon with nitrogen dioxide ($NO_2$) preferably in the presence of oxygen and/or water.

The process of homogeneous nitration is generally performed by initially preheating the reactants before they are carried into the reaction zone. The preheating conditions are preferably substantially the same temperature and pressure as the reaction conditions, as fully described below.

The reactant feed of the present process can be selected from an aliphatic or an aliphatic-aromatic olefinic unsaturated hydrocarbon. The term "olefinic unsaturated hydrocarbon" or "olefinic unsaturated compound" as used in the present disclosure and in the claims appended hereto refers to aliphatic compounds having at least one (preferably one) carbon to carbon double bond and from three to twelve carbon atoms. The term also refers to aliphatic-aromatic compounds having eight to twelve carbon atoms, an aromatic ring and a hydrocarbon side chain which contains a carbon to carbon double bond, preferably at its terminal position. The preferred olefinic unsaturated hydrocarbons are aliphatic compounds having a single carbon to carbon double bond. In view of nitromethane being a very commercially important product, the most preferred compounds have a structure such that at least one methyl group is covalently bonded to a carbon atom of an olefinic group as, for example, propylene or 1,1-dimethyl ethylene and the like.

The olefinic unsaturated hydrocarbons which are useful as starting reactant in the present process can be represented by the general formula

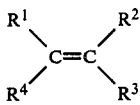

whereby when $R^1$ represents an alkyl group, $R^2$, $R^3$ and $R^4$ each separately represent hydrogen or an alkyl group provided that the sum of the carbon atoms of the alkyl groups $R^1$, $R^2$, $R^3$ and $R^4$ is from 1 to 10, preferably from 1 to 6 carbon atoms. Although the aklyl groups represented by any of the $R^1$, $R^2$, $R^3$ and $R^4$ may be different from each other, it is preferred that all such alkyl groups be the same to provide a single nitroalkane as the sole or predominant product. It is also preferred that any alkyl group be selected from a $C_1$–$C_5$ alkyl group, most preferably a methyl group as the resultant product, nitromethane, is a highly desired commercial compound.

The above general formula can also represent useful starting reactants which have a phenyl group therein. These reactants are represented by the above general formula when $R^1$ is a phenyl ($C_6H_5$—) group or a $C_7$–$C_{10}$ aralkyl group and $R^2$, $R^3$ and $R^4$ are hydrogen.

The particular structure of the olefinic unsaturated hydrocarbon used as the feed in the subject process will be the determinative element as to which nitro compound is formed or what predominant nitro compound is formed from a mixture. For example, when the olefinic unsaturated hydrocarbon is represented by $$R^1-CH=CH_2$$

wherein $R^1$ represents an alkyl, aryl or aralkyl group, $R^1NO_2$ will be the sole or dominant product formed. When the olefinic unsaturated hydrocarbon is represented by the general formula

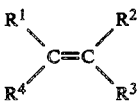

as described herein above in which $R^1$ represents an alkyl, aryl or aralkyl group and $R^2$, $R^3$ and $R^4$ each represent a hydrogen atom or the same group as $R^1$, then $R^1NO_2$ will be the sole or dominant product. When $R^1$ and any one or more of the $R^2$, $R^3$ and $R^4$ groups represent different alkyl groups as provided in the above definitions, the products will be a mixture of nitroalkanes $R^1NO_2$, $R^2NO_2$, $R^3NO_2$ and $R^4NO_2$.

As stated above, the most preferred olefinic unsaturated hydrocarbon to be used in the present process is propylene ($R^1$ is $CH_3$ and $R^2$, $R^3$ and $R^4$ are each hydrogen) because it is readily available, inexpensive and forms the most desired nitroalkane, nitromethane.

The olefinic unsaturated hydrocarbon compounds preferably do not contain non-hydrocarbon groups. However, the compounds may contain non-hydrocarbon groups which will not inhibit the subject process, such as nitriles and the like.

The above described olefinic unsaturated hydrocarbons are contacted in vapor phase in the reaction zone with nitrogen dioxide. The nitrogen dioxide can be supplied as $NO_2$ or in the form of its precursors, $N_2O_4$ or nitric acid which dissociates to $NO_2$ and water under the reaction zone conditions. These materials are readily obtained commerically.

It is preferred that the feed also includes oxygen, usually in the form of air. The oxygen as well as the nitrogen dioxide can be at least partially obtained from recycled unreacted materials which have been separated and purified by conventional methods from the reaction product as more fully described below.

The feed may further contain inert gas such as nitrogen, carbon monoxide, carbon dioxide, argon or mixtures thereof. Further, the feed can contain water either as part of the carrier for the olefinic unsaturated hydrocarbon reactant feed or as a part of the nitrating agent.

The conditions and parameter ranges for conducting the homogeneous gaseous nitration of an olefinic unsaturated hydrocarbon are (a) that the reaction zone feed be in a molar ratio of $NO_2$ to olefinic unsaturated hydrocarbon of from about 0.1 to 4 or greater and preferably from about 0.1 to 2 with low ratios being most preferred. The environment can be, therefore, either a reducing or an oxidizing environment depending on the feed ratio used. When oxygen is used as an additional feed, it should be in from about 0.05 to 1 mole per mole of $NO_2$. The reaction is carried out at elevated temperature of from about 100° to about 500° C. and preferably from about 250° to 350° C. The reaction is carried out under elevated pressure of from about 2 to 20 bars with from 5 to 12 bars being preferred. The pressure must be elevated and the combined temperature and pressure conditions must be such as to maintain the reactants in a homogeneous gas phase. The inert gases in the feed (A, CO, $CO_2$, $N_2$) can be from about 0 to 90 volume percent. The water can be from about 0 to 30 weight percent based on the $NO_2$ with at most 10 being preferred. The reaction contact time of the reaction gases in the reaction zone can be from aobut 0.5 to 20 seconds with the order of from about 1 to 10 seconds being preferred.

Referring to the drawing to illustrate the subject process, an olefinic unsaturated hydrocarbon such as propylene is transported from a reservoir (not shown) by pipeline 1 to preheater 2. The preheater is maintained at substantially the reaction zone entry temperature of about 100° to 500° C. and pressure of from about 2 to 20 bars. The preheated olefinic unsaturated hydrocarbon is then passed through pipeline 4 to reactor intake pipeline 5. The nitrogen dioxide and the oxygen (as air, when used) are introduced to preheater 8 via pipelines 6 and 7, respectively. The preheater 8 is maintained at temperature and pressure conditions substantially the same as that of preheater 2. The mixed preheated $NO_2/O_2$ gases pass through pipeline 9 to reactor intake pipeline 5 using gas-gas mixing devices such as spargers, venturis, etc. The preheated gases are passed through reactor 10 which may be in the form of a tubular reactor heated by salt at a temperature of from 100° to 500° C., preferably from 250° to 350° C. and at a pressure of approximately 2 to 20, preferably about 5 to 12 bars. The reactor effluents withdrawn through pipeline 11 are cooled to ambient temperature in cooler 12 which uses super-cooled water to rapidly cool the gases. The cooled reactor effluents are separated in the separator 13. The liquid effluent separates into organic liquid phase 14 and aqeuous liquid phase 15.

The uncondensed gaseous reaction effluents are removed from the separator 13 through pipeline 16. The uncondensed gaseous reaction effluents are a mixture of components composed predominantly of unreacted olefinic unsaturated hydrocarbon feed (e.g. propylene), nitric oxide and inert gases. These gaseous reaction effluents are then treated at station 17 in one of a variety of conventional manners before recycling back through reactor intake pipeline 5 as part of the feed to reactor 10. The specific modes of treatments chosen do not effect the present invention. For illustrative purposes, the gaseous effluent can be treated (a) by directly injecting oxygen into the gaseous effluent to re-oxidize the nitric oxide to nitrogen dioxide; (b) by cryogenically removing any of the olefinic unsaturated hydrocarbon gases contained in the gaseous effluent prior to oxidizing the nitric oxide; or (c) by removing the nitric oxide from the gaseous effluent by absorption in ferrous sulfate solution and subsequent stripping followed by re-oxidizing the nitric oxide to nitrogen dioxide. To prevent build-up of inert gases due to the recycling of treated gaseous effluent, a purge stream 18 is maintained.

The condensed organic and aqueous liquid phases 14 and 15, respectively, are removed from separator 13 and sent by pipelines 14¹ and 15¹ to an azeotropic distillation column 19. When the nitro compound product has a lower density than water (i.e. some C₄ and higher nitro compounds) the organic and aqueous liquid phases 14 and 15 will be reversed position in separator 13 to that shown. In such instances (not shown) line 14¹ will enter the bottom portion of column 19 and line 15¹ will enter the top portion of column 19. Azeotropic distillation column 19 normally operates at a pressure of about 1.25 bars or less and at temperatures sufficient to azeotropically distill the nitroalkane or nitroaromatic products as well as other compounds having a boiling point lower than the nitro products, including reaction zone by-product oxygenated hydrocarbon with associative water. These materials are passed via pipeline 20, condenser 21 and pipeline 22 to a light oxygenate removal distillation column 25. Some of the distillate may be recycled to the azeotropic column 19 by pipeline 23. The majority of the water and the heavy by-products such as acids and the like are removed as bottom products through pipeline 24.

The oxygenate removal column 25 operates at a pressure of about 1.25 bars or less and at a temperature range sufficient to remove overhead any oxygenated hydrocarbon by-products such as a temperature range of from 30° C. to 95° C. The bottom product of column 25 is removed by pipeline 26 and is composed of the nitrohydrocarbon product in the form of a single nitroalkane or nitroaromatic or mixture of nitroalkanes or nitroaromatic as is appropriate based on the olefinic unsaturated hydrocarbon feed used. In addition there may be present a small amount of water (from the prior azeotropic distillation) and trace amounts of oxygenated hydrocarbon by-products. The material removed by pipeline 26 is subsequently chemically treated (not shown) to remove any trace oxygenated contaminants then fed to a dehydration column (not shown) and where a mixture of nitrocompounds are produced to a fractionation column (not shown) to recover pure nitro products. The nitro product of the present process is either composed of a single nitro compound such as nitromethane or of a mixture of nitro compounds highly selective with respect to one nitro product which is dependent on the starting olefinic unsaturated hydrocarbon feed.

The overhead effluent of column 25 is removed by pipeline 27 through condenser 28. Some of the distillate may be recycled to column 25 by pipeline 29. The overhead distillate is normally small in comparison to the bottom product and is made up predominantly of oxygenated hydrocarbons. These can be incinerated or recycled via pipeline 30 to preheater 2 and incorporated as part of the olefinic unsaturated hydrocarbon feed.

It has been unexpectedly found that one can readily form nitroalkane or nitroaromatic compounds by utilizing an olefinic unsaturated hydrocarbon as the feed material in a homogeneous gas phase process. The nitro compound produced will be highly selective based on the particular olefinic unsaturated hydrocarbon used as the feed and that one obtains the nitrohydrocarbon product in higher yields than obtainable by conventional solution methods. Further, the subject process provides a means of custom directing the formation of a preselected nitro compound. Although olefinic hydrocarbons have been used as reactants in solution processes as described above, they are known to provide low yields and low selectivity of nitroalkane products. For this reason those skilled in the art have not heretofore contemplated olefinic compounds as being a useful starting reactant in any process.

The following examples are given for illustrative purposes only and are not meant to be a limitation on the claims appended hereto. All parts and percentages are by weight unless otherwise indicated.

EXAMPLE I

A series of production runs were conducted using propylene as the olefinic unsaturated hydrocarbon feed. Each feed material was preheated to 200° C. at 10 bars. The nitrogen dioxide and oxygen (when used) were preheated separately from the propylene and water (when used). The preheated feed materials were then mixed and reacted in a tubular reactor for the indicated residence time. The reactor effluent was quenched. The nitric oxide, carbon monoxide and carbon dioxide were removed and the nitric oxide treated with oxygen to obtain nitrogen dioxide which was recycled to the reactor. The remaining liquid was distilled to azeotropically remove the nitro compound and low boiling by-product oxygenated hydrocarbon. The azeotropic distillate was further distilled to separate the nitro compound from the oxygenates. The nitro compound was predominantly nitromethane.

Table I below summarizes the reaction condition, feeds and products. All entries are given in mmoles per hour. The yield of nitromethane is based on moles of nitro compound per total moles of non-recyclable products.

TABLE I

| NITRATION OF PROPYLENE | | | | |
|---|---|---|---|---|
| Run No. | 1 | 2 | 3 | 4 |
| Temperature (°C.) | 300 | 300 | 300 | 270 |
| Pressure (atm) | 10 | 10 | 10 | 10 |
| Residence Time (sec.) | 7.0 | 6.1 | 5.7 | 6.2 |
| Feed (mmoles/hr) | | | | |
| Propylene | 1967 | 2503 | 2479 | 6435 |
| Oxygen | 0 | 297 | 297 | 297 |
| Water | 0 | 0 | 771 | 788 |
| Nitrogen | 8020 | 8666 | 8666 | 4331 |
| Nitrogen Dioxide | 889 | 1139 | 1236 | 1295 |
| $NO_2/C_3H_6$ | 0.45 | 0.45 | 0.49 | 0.20 |
| Carbon Selectivity (%) | | | | |
| Nitromethane | 14.1 | 11.4 | 12.2 | 18.5 |
| Nitroethane | 0 | 0 | 0 | 0 |
| 1-Nitropropane | 0 | 0 | 0 | 0 |
| 2-Nitropropane | 1.1 | 0.8 | 0.9 | 0.8 |
| Formic Acid | 6.9 | 12.7 | 7.8 | 6.5 |

TABLE I-continued

| NITRATION OF PROPYLENE | | | | |
|---|---|---|---|---|
| Run No. | 1 | 2 | 3 | 4 |
| Acetic Acid | 0 | 0.6 | 2.9 | 0.6 |
| Ethanol | 0.4 | 0.6 | 2.5 | 4.1 |
| Acetaldehyde | 11.1 | 9.5 | 9.7 | 24.5 |
| Acetone | 3.6 | 2.2 | 3.0 | 1.6 |
| Nitrile | 12.0 | 7.1 | 8.1 | 8.7 |
| Nitrite | 2.2 | 3.1 | 4.1 | 7.5 |
| CO | 14.3 | 14.5 | 13.3 | 7.9 |
| $CO_2$ | 34.5 | 37.7 | 35.2 | 19.3 |
| Carbon Conversions (%) | 9.0 | 11.9 | 13.5 | 5.6 |

EXAMPLE II

A series of production runs were conducted in the same manner as in Example I above except that instead of propylene, 1-butene, 2-butene and isobutene were each used as the olefinic unsaturated hydrocarbon. The reaction conditions, feeds and products are listed in table II below. The yield was based on a per pass run.

TABLE II

| BUTENE NITRATION | | | |
|---|---|---|---|
| Run No. | 1 | 2 | 3 |
| Temperature (°C.) | 300 | 300 | 300 |
| Pressure (atm) | 10 | 10 | 10 |
| Residence Time (sec.) | 5.6 | 5.6 | 2.9 |
| Feed (mmoles/hr) | | | |
| 2-Butene | 1750 | 0 | 0 |
| 1-Butene | 0 | 1950 | 0 |
| Isobutene | 0 | 0 | 1320 |
| Nitrogen Dioxide | 1933 | 1905 | 1816 |
| Nitrogen | 9793 | 9793 | 9793 |
| Carbon Selectivity (%) | | | |
| Nitromethane | 6.7 | 2.7 | 2.8 |
| Nitroethane | 1.0 | 12.4 | 0 |
| 1-Nitropropane | 0 | 3.5 | 0 |
| Acetaldehyde | 39.3 | 3.6 | 0.4 |
| Paraldehyde | 12.6 | 0 | 0 |
| Propionaldehyde | 0 | 10.5 | 0 |
| Acetone | 0 | 0 | 50.7 |
| Acetonitrile | 7.2 | 1.6 | 0 |
| Propionitrile | 0 | 10.5 | 0 |
| CO | 7.6 | 21.2 | 17.8 |
| $CO_2$ | 21.6 | 27.6 | 21.0 |
| Carbon Conversion (%) | 18.1 | 14.3 | 30.0 |

While the invention has been described in connection with certain preferred embodiments, it is not intended to limit the invention to the particular form set forth, but, on the contrary, it is intended to cover such alternatives, modifications and equivalents as defined by the appended claims.

What is claimed is:

1. A process for selectively forming nitroalkanes and nitroaromatics comprising contacting in a reaction zone at an elevated pressure of from about 2 to 20 bars and a temperature of from about 100° C. to 500° C. in a homogeneous gas phase, nitrogen dioxide or nitric acid or both with an olefinic unsaturated hydrocarbon represented by the formula

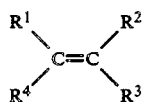

whereby when $R^1$ represents an alkyl group, $R^2$, $R^3$ and $R^4$ each separately represent hydrogen or an alkyl group such that the sum of the carbon atoms of $R^1$, $R^2$, $R^3$ and $R^4$ is up to 10 or whereby when $R^1$ represents a phenyl or a $C_7$–$C_{10}$ aralkyl group, $R^2$, $R^3$ and $R^4$ are hydrogen; and recovering the formed dominant nitrocompound $R^1NO_2$ whereby $R^1$ represents the same group as for the olefinic hydrocarbon defined above and when $R^2$, $R^3$ or $R^4$ represent an alkyl, additionally recovering the respective nitrocompounds $R^2NO_2$, $R^3NO_2$ and $R^4NO_2$.

2. The process of claim 1 wherein the olefinic unsaturated hydrocarbon is an alkene in which $R^1$ is an alkyl and $R^2$, $R^3$ and $R^4$ each separately represent hydrogen or an alkyl and the sum of the carbon atoms of $R^1$, $R^2$, $R^3$ and $R^4$ is 1–6.

3. The process of claim 2 wherein the olefinic unsaturated hydrocarbon is selected from propylene, 1-butene, 2-butene, or isobutene.

4. The process of claim 3 wherein the process further comprises cooling the reaction zone effluent, separating the resulting liquid phase effluent from the non-condensed gaseous effluent and recovering any oxygenated hydrocarbon and returning at least a portion of said oxygenated hydrocarbon to the reaction zone.

5. The process of claim 2 wherein the process further comprises cooling the reaction zone effluent, separating the resulting liquid phase effluent from the non-condensed gaseous effluent and recovering any oxygenated hydrocarbon and returning at least a portion of said oxygenated hydrocarbon to the reaction zone.

6. The process of claim 1 wherein the olefinic unsaturated hydrocarbon has an $R^1$ group representing a phneyl or $C_7$–$C_{10}$ aralkyl group and $R^2$, $R^3$ and $R^4$ each represent a hydrogen atom.

7. The process of claim 6 wherein the process further comprises cooling the reaction zone effluent, separating the resulting liquid phase effluent from the non-condensed gaseous effluent and recovering any oxygenated hydrocarbon and returning at least a portion of said oxygenated hydrocarbon to the reaction zone.

8. The process of claim 1 wherein the process further comprises cooling the reaction zone effluent, separating the resulting liquid phase effluent from the non-condensed gaseous effluent and recovering any oxygenated hydrocarbon and returning at least a portion of said oxygenated hydrocarbon to the reaction zone.

9. The process of claim 1 wherein the reaction zone further contains oxygen, water or both.

10. The process of claim 9 wherein the olefinic unsaturated hydrocarbon is an alkene in which $R^1$ is an alkyl and $R^2$, $R^3$ and $R^4$ each separately represent hydrogen or an alkyl and the sum of the carbon atoms of $R^1$, $R^2$, $R^3$ and $R^4$ is 1–6.

11. The process of claim 10 wherein the olefinic unsaturated hydrocarbon is selected from propylene, 1-butene, 2-butene, or isobutene.

12. The process of claim 11 wherein the process further comprises cooling the reaction zone effluent, separating the resulting liquid phase effluent from the non-condensed gaseous effluent and recovering any oxygenated hydrocarbon and returning at least a portion of said oxygenated hydrocarbon to the reaction zone.

13. The process of claim 12 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

14. The process of claim 11 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

15. The process of claim 10 wherein the process further comprises cooling the reaction zone effluent, separating the resulting liquid phase effluent from the noncondensed gaseous effluent and recovering any oxygenated hydrocarbon and returning at least a portion of said oxygenated hydrocarbon to the reaction zone.

16. The process of claim 15 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

17. The process of claim 10 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

18. The process of claim 9 wherein the olefinic unsaturated hydrocarbon has an $R^1$ group representing a phenyl or $C_7$–$C_{10}$ aralkyl group and $R^2$, $R^3$ and $R^4$ each represent a hydrogen atom.

19. The process of claim 8 wherein the process further comprises cooling the reaction zone effluent, separating the resulting liquid phase effluent from the noncondensed gaseous effluent and recovering any oxygenated hydrocarbon and returning at least a portion of said oxygenated hydrocarbon to the reaction zone.

20. The process of claim 19 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

21. The process of claim 18 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

22. The process of claim 9 wherein the process further comprises cooling the reaction zone effluent, separating the resulting liquid phase effluent from the oxygenated hydrocarbon and returning at least a portion of said oxygenated hydrocarbon to the reaction zone.

23. The process of claim 22 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

24. The process for claim 9 wherein the reaction zone pressure is from about 5 to 12 bars, temperature is from about 250° to 350° C., the $O_2$ to $NO_2$ or $HNO_3$ molar ratio is from about 0.05 to 1 and the $NO_2$ or $HNO_3$ to olefinic unsaturated hydrocarbon molar ratio is from about 0.1 to 2.

* * * * *